United States Patent [19]

Cahoon

[11] Patent Number: 5,616,493
[45] Date of Patent: Apr. 1, 1997

[54] METHOD FOR FOAM BIOPROCESS

[76] Inventor: Richard S. Cahoon, 68 Spring Run Rd., Freeville, N.Y. 13068

[21] Appl. No.: 426,193

[22] Filed: Apr. 21, 1995

[51] Int. Cl.$^6$ ................................................. C12N 1/00
[52] U.S. Cl. ................................... 435/246; 435/261
[58] Field of Search ................................ 435/246, 247, 435/250, 255.7, 261, 812

[56] References Cited

U.S. PATENT DOCUMENTS

| | | | |
|---|---|---|---|
| Re. 30,543 | 3/1981 | Hitzman et al. | 435/246 |
| 3,186,959 | 6/1965 | Shriver et al. | 261/DIG. 26 |
| 3,677,895 | 7/1972 | Hashimoto | 435/246 |
| 4,340,677 | 7/1982 | Hitzman | 435/246 |
| 4,654,305 | 3/1987 | Barnett et al. | 435/246 |
| 5,021,069 | 6/1991 | Whellock et al. | 435/282 |
| 5,266,481 | 11/1993 | Wegner et al. | 435/246 |

*Primary Examiner*—George Yeung
*Attorney, Agent, or Firm*—Nixon, Hargrave, Devans & Doyle

[57] ABSTRACT

A biological process includes the step of producing a substantially continuous foam of gas bubbles in a liquid capable of undergoing a biological process utilizing prokaryotic or eukaryotic cells. The cells are introduced into the foam after the foam is produced and maintained in the foam under conditions effective to carry out the process. A reaction product of a biological process utilizing a foam culture medium is recovered by subjecting the foam to a pressure change after maintaining the cells in the foam culture medium under conditions effective to sustain the process. An apparatus for carrying out a biological process includes a foam production chamber having one or more inlets for introducing a gas and components of a culture medium. The chamber is adapted for producing a foam of bubbles of the gas in the culture medium. A plug-flow reactor is positioned to receive foam from the foam production chamber as a continuously-flowing plug. The apparatus further includes means for introducing cells into the plug-flow reactor.

21 Claims, 5 Drawing Sheets

METHOD FOR FOAM BIOPROCESS

FIELD OF THE INVENTION

The present invention relates to a biological process utilizing biological cells, and more particularly to a method and apparatus for carrying out a biological process in a foam comprising prokaryotic or eukaryotic cells.

BACKGROUND OF THE INVENTION

Biological processes, specifically processes involving cells maintained in a fluid environment, are of increasing importance, because they are the means by which the unique synthetic and catalytic capabilities of prokaryotic and eukaryotic cells are put to work in manufacturing and other industrial processes. Examples of such processes include the production of proteins, antibodies, and other molecules useful, for example, in pharmaceutical applications and waste treatment processes, and industrial products, such as, for example, materials produced for foods, chemical processing, and agriculture, etc. Examples of such industrial products include enzymes for the textile, food, pulp and paper industries; feedstocks for chemical processes, such as acetone, butanol, ethanol, and acetic acid; biopolymers such as guar and carrageenan in foods and degradable packaging; dyes; flavors and fragrances; bioadhesives; and bioadsorbants and supports, for example, chitin.

Biological cells must be surrounded by water, and require nutrients (e.g., carbon, hydrogen, phosphorus, potassium, nitrogen, sulfur, calcium, iron, magnesium, manganese, boron, copper, and others), electron acceptors (oxygen for aerobes, e.g., nitrate or sulfate for anaerobes) and electron donors (e.g., carbohydrates). "Bioreactors" that contain and support bioprocesses, are designed to maintain appropriate process conditions, such as temperature, as well as nutrient supply and waste removal. Traditionally, biological cells have been submerged in vats or tanks of aqueous nutrient medium. However, such bioreactors are limited in their ability to efficiently facilitate the mass transport of nutrients and waste products, particularly gases, to and from biological cells. The delivery of sufficient oxygen from outside the bioreactor to meet the high oxygen demand of some processes is particularly problematic in such submerged tank reactors.

One common type of submerged tank bioreactor is the continuous stirred tank reactor (CSTR). The CSTR is essentially a closed, cylindrical vat with a vertical shaft projecting through the top or bottom with paddles attached. Rotation of the shaft stirs the bioreactor contents (aqueous medium and cells) and accomplishes mass transport through mechanical agitation. Cells are suspended in aqueous medium, and oxygen is delivered to the cells by a combination of gas injection and stirring by the revolving paddles.

There is significant potential for medium contamination in the CSTR, however. The seals for the rotating shaft are the primary route for the introduction of external contaminants into axenic cultures. In addition, control of heat transfer (for example, cooling fermentation broths which overheat due to the heat of metabolism) can be difficult. Oxygen delivery to the cells is also generally inefficient, as noted above. In order to transport sufficient oxygen to aerobic cells, the medium must be vigorously stirred. The resulting shear forces generated by the revolving paddles cause cell trauma, senescence, and often death. The dilemma is that many cells, particularly mammalian cells, which are sensitive to shear and which require high levels of oxygen, will die in high-shear environments; however, the same cells will die of anoxia if shear forces are reduced to tolerable levels. Also, the high energy input required for gas injection, mechanical stirring, and cooling of a CSTR is expensive.

Various bioprocess systems and reactor designs have been developed to solve this problem, including fixed film reactors and bubble columns. In fixed film reactors, cells are fixed to a surface and are stationary while the medium moves past them. In bubble columns, downward falling cells are suspended in medium by upward moving gas bubbles, and the bubble movement results in mass transfer of the gas in the bubbles. In these systems, shear is lower than in CSTRs, but the surface area of contact between the cells and the gas phase is a rate limiting factor.

In order to overcome the limitations of these processes, a number of methods for carrying out biological processes in foams have been developed. These processes employ foams that are essentially reticulated networks of gas/fluid interfaces of high surface area as the culture medium for cells, which are present in the liquid thin film with the reactants of a desired bioprocess reaction. Because the cells are proximal to the gas interface, improved mass transport rates and, therefore, faster process rates, with less energy input, can be achieved.

U.S. Pat. No. 3,677,895 to Hashimoto ("Hashimoto") describes a process for reacting paraffinic hydrocarbons with microbial cells to produce protein in a CSTR. The culture medium is an aqueous foam comprising a discontinuous gas phase with oxygen or a gaseous hydrocarbon and a continuous aqueous interface surrounding the gaseous reactant with nutrients, microorganisms, and foam stabilizers to maintain the foamed state. Hashimoto discloses batch, CSTR type reactors, and a centrifuge is used following fermentation to separate the microorganisms from the medium.

U.S. Pat. Nos. Reissue 30,543 and U.S. Pat. No. 4,340,677 to Hitzman, et al. ("Hitzman I") and Hitzman ("Hitzman II"), respectively, each relate to fermentation processes in a foam. The reactors disclosed are essentially batch reactors, although Hitzman I describes carrying out both "batch" and "continuous" fermentation processes. In the continuous process, oxygen or air, nutrient medium, and alcohol are continuously introduced into the reactor throughout the process run. Hitzman I and II each employ mechanical foam breakers.

Pumped loop reactors for carrying out bioprocesses utilizing foams are described in U.S. Pat. No. 5,021,069 to Whellock, et al. ("Whellock"). Whellock is primarily concerned with bioleaching processes, where the relatively high turbulence and shear conditions maintained in the reactor columns are desirable.

High shear forces are present, however, in the foam bioprocesses of Hashimoto, Hitzman I and Hitzman II, as well. The production of foam in cell-containing medium by mechanical stirring and/or rapid injection of gas exerts potentially harmful shear forces on delicate cells, as does the breaking of foam by with, for example, rotating surfaces as in Hitzman II. Cell trauma and death resulting from these forces limit process rates and yields, and increase the cost of many processes. The present invention is directed to overcoming the deficiencies in the art.

SUMMARY OF THE INVENTION

The present invention is directed to a biological process utilizing a substantially continuous foam. The foam contains bubbles in a liquid capable of undergoing a biological process utilizing cells. The cells are introduced into the process after the foam is formed and are maintained in the foam under conditions effective to carry out the biological process.

Another aspect of the present invention relates to the recovery of a reaction product from a biological process utilizing a substantially continuous foam containing cells. After the process is completed, the foam is subjected to a pressure change to collapse the foam, and the reaction product is then separated from the culture medium.

The invention further includes an apparatus for carrying out a biological process utilizing a substantially continuous foam. A foam production chamber having one or more inlets for introducing a gas and the components of a culture medium is adapted for producing a foam comprising bubbles of the gas in the medium. A plug-flow reactor is positioned to receive foam from the foam production chamber as a continuously flowing plug. The apparatus further includes means for introducing cells into the plug-flow reactor.

By employing separate foam production and cell entrainment steps in the method of the present invention, cells are kept out of a high shear environment. This is particularly important in processes employing plant, mammalian, or other animal cells. Similarly, by employing a change in pressure to collapse a foam culture medium, the method of the present invention provides a low shear alternative to prior, mechanical foam-breaking techniques.

In the apparatus of the present invention, foam production and cell entrainment are spatially and temporally separated, to minimize shear forces experienced by the cells. This is superior to prior foam bioprocesses, in which foam is generated in culture medium containing the microorganism participating in the biological process.

DETAILED DESCRIPTION OF THE INVENTION

As described above, the present invention is directed to a biological process utilizing a substantially continuous foam. The foam contains bubbles in a liquid capable of undergoing a biological process utilizing cells. The cells are introduced after the foam is formed and are maintained in the foam under conditions effective to carry out the biological process.

Another aspect of the present invention relates to the recovery of a reaction product from a biological process utilizing a substantially continuous foam containing cells. After the process is completed, the foam is subjected to a pressure change to collapse the foam, and the reaction product is then separated from the culture medium.

The invention further includes an apparatus for carrying out a biological process utilizing a substantially continuous foam. A foam production chamber having one or more inlets for introducing a gas and the components of a culture medium is adapted for producing a foam comprising bubbles of the gas in the medium. A plug-flow reactor is positioned to receive foam from the foam production chamber as a continuously flowing plug. The apparatus further includes means for introducing a cells into the plug-flow reactor.

Figure 1A:
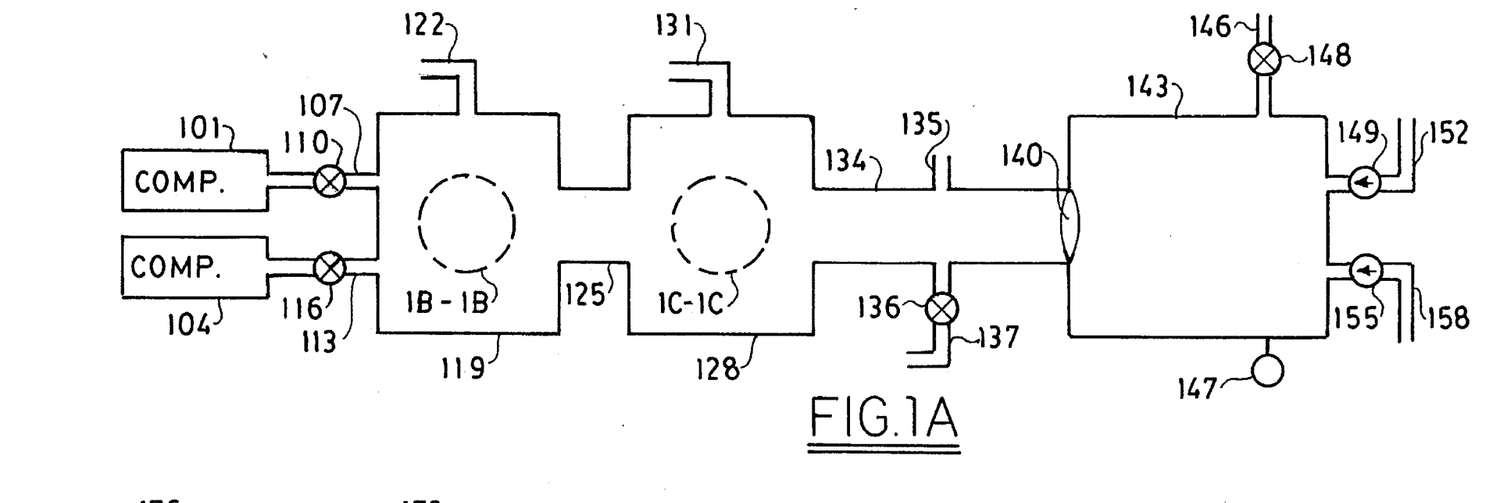
FIG. 1A is a schematic view of a bioreactor apparatus according to the present invention.

As shown in FIG. 1A, gases from compressors 101 and 104, which could, alternatively, be gas cylinders, are fed via valves 110 and 116, respectively, through lines 107 and 113 into foam production chamber 119. As described more fully below, the gases employed can be one or several gases, including, for example, air, oxygen, or methane. Aqueous medium, and/or individual medium components such as foam stabilizers, nutrients, surfactants, etc., as discussed below, are added through one or more inlets 122. Foam is produced in foam production chamber 119 through vigorous agitation of the medium or vigorous injection of gases from compressors or cylinders 101 and 104, as discussed below.

As foam production continues, foam advances through conduit 125 into cell entrainment chamber 128. The prokaryotic or eukaryotic cells to be employed in the biological process are introduced into chamber 128 via line 131.

Cell-containing foam then advances essentially unmixed through plug-flow reactor 134 as a substantially continuous plug. Optionally, excess gas may be released through vent 135. Process wastes or products can be removed from reactor 134 via valve 136 and line 137.

In the plug-flow reactor, the foam, containing necessary components for the desired biological process to occur, physically moves away from the cell entrainment stage of the reactor through a spatially-distinct reaction phase as an essentially stable foam. In the foam, the number and size of the bubbles remain essentially constant as the foam moves through the reactor.

Following progression of the foam through reactor 134, foam enters foam-collapse chamber 143 via valve 140. A pump, for example a pulsed-diaphragm pump, may be employed in place of valve 140. The foam is then subjected to a pressure increase or decrease in chamber 143 to collapse the foam. Vacuum may be pulled on the contents of chamber 143 via line 146 connected to a vacuum pump (not shown). Alternatively, chamber 143 may be pressurized via a line connected to a cylinder or compressor (not shown). In either case, the rate of pressure change may be monitored via gauge 147 and controlled via valve 148 to avoid the exertion of stress on the cells.

Following collapse of the foam, cells or reaction products are recovered from chamber 143 via lines 152 and 158 which are suctioned via pump inlets 149 and 155, respectively. The reaction medium may be pumped to a separation device, such as a centrifuge, or gravity separation of the reaction medium components may be carried out, either within chamber 143 or another vessel to which the contents of chamber 143 have been transferred.

Figure 1B:
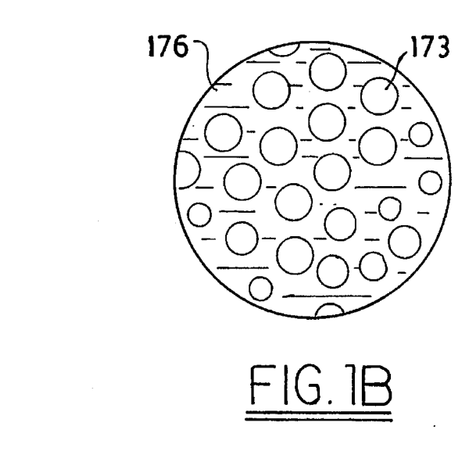
FIGS. 1B and 1C are enlarged sectional views of segments of the foam contained in different stages of the apparatus of FIG. 1A.

FIG. 1B is a schematic view of a section of the foam in foam production chamber 119. In the foam, liquid medium 176 surrounds discontinuous gas phase 173.

Figure 1C:
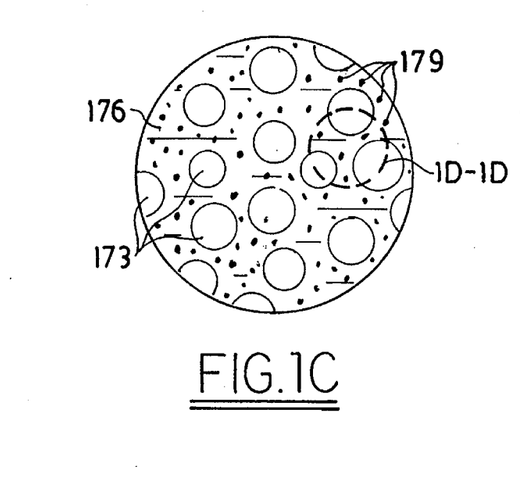
Figure 1D:
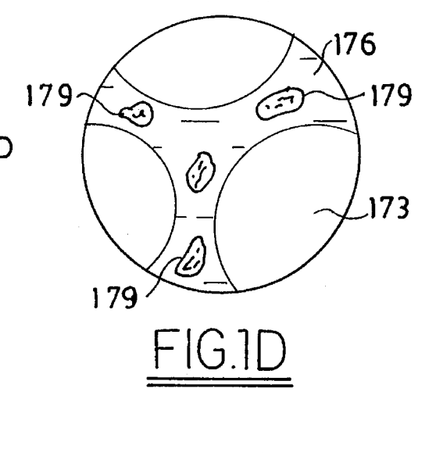
FIG. 1D is an enlarged sectional view of a segment of the foam shown in FIG. 1C.

FIG. 1C is a schematic view of a section of the cell-containing foam in cell entrainment chamber 128. Prokaryotic or eukaryotic cells 179 are maintained in a continuous film of liquid medium 176 which surrounds discontinuous gas phase 173. FIG. 1D is an expanded view of a section of the foam shown in FIG. 1C. FIGS. 1C and 1D illustrate how the cells remain bathed in the nutrient- and reactant-containing aqueous environment, but remain physically very close to the gas phase. This physical proximity results in high mass transport rates of gas to and from the cell without high shear. This arrangement of continuous liquid phase and discontinuous gas phase also permits homogeneous distribution of cells throughout the foam.

Foams of very high interfacial gas/liquid surface area can be created and since interfacial surface area is a key variable in mass transport rate and mass transport rate is a key variable in overall bioprocess rate, such high interfacial areas will result in much increased bioprocess rate.

In the foam collapse process shown in FIG. 1A, the discontinuous gas phase, surrounded by the continuous liquid phase, is completely disrupted by the application of a pressure differential. As noted above, this pressure differential may be designed to increase or decrease the pressure on the gas bubble relative to the bubble's internal pressure. For certain fragile cells, gradual bubble collapse (implosion) is required. In this case, the biofoam destruction step is the application of higher pressure. For other, less fragile cells, bubble explosion is acceptable, in which case, the biofoam is subjected to a vacuum.

The breakage of the biofoam is very important since it has been shown that bubble bursting can be a cause of cellular trauma. Collapse of the foam transforms it into distinct phases of liquid, gas, cells and related biomass, providing the opportunity to further separate these phases and constituents.

As will be apparent to those skilled in the art, alternatives to the particular embodiment shown in FIG. 1A may be employed. For example, for some biological processes, only one gas compressor or cylinder may be employed. Other processes may employ more than two cylinders or compressors.

Figure 2A:
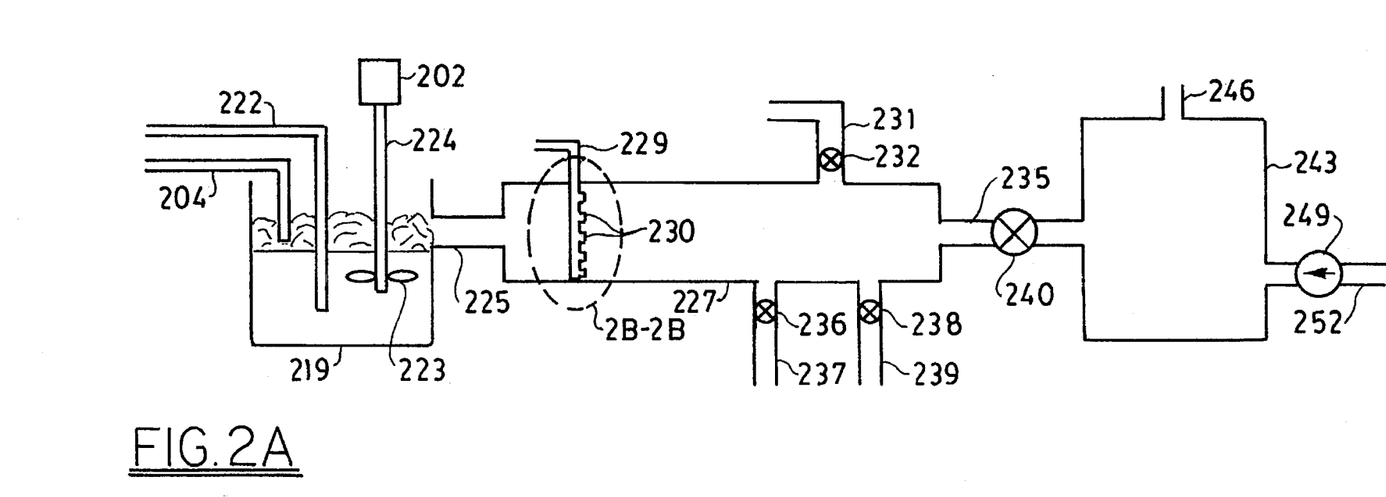
FIG. 2A is a schematic view of an alternative embodiment of a bioreactor apparatus in accordance with the present invention.

An alternative embodiment of the present invention is shown in FIG. 2A. Here, a foamed aqueous medium is created in foam production chamber 219 by the vigorous introduction of gas via line 222 or by vigorous agitation of the medium by rotation of impeller 223 rotated on shaft 224 by motor 202. Medium is introduced via one or more inlet lines 204. Foam created in chamber 219 advances via conduit 225 into plug-flow reactor 227

FIG. 2A further illustrates an alternative method of effectively distributing cells in the foam medium via cell distribution manifold 229 having cell emitters 230. As described with respect to FIG. 1A, additional medium components may be added through line 231 via valve 232. Any waste products which migrate due to gravity to the bottom of the reactor may be removed through lines 237 and 239 via valves 236 and 238, respectively. The foam then advances out of plug-flow reactor 227 via tube 235 into the foam collapse chamber 243. Entry of foam into chamber 243 may be controlled via valve 240. Pressure change may be exerted on the foam in chamber 243 via line 246 connected to either a source of vacuum or pressure as has been described in connection with FIG. 1A. Reaction product may be removed via line 252 fitted with valve 249.

Figure 2B:
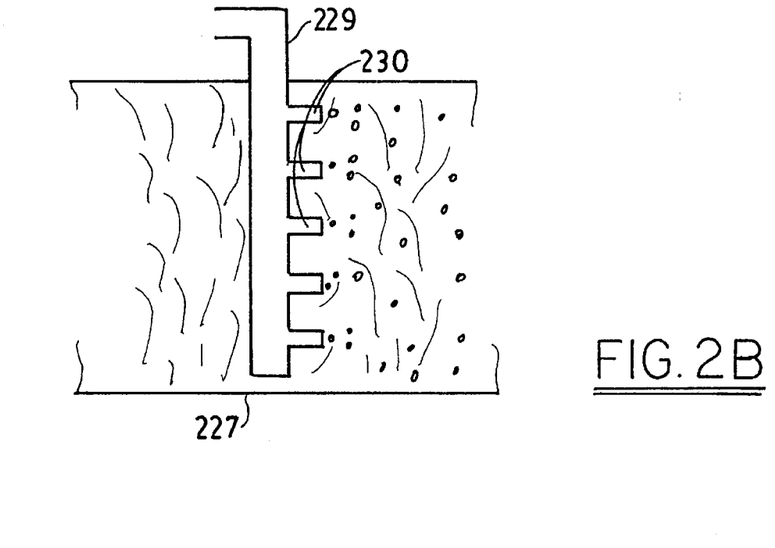
FIG. 2B is an enlarged view of the cell entrainment portion of the bioreactor apparatus shown in FIG. 2.

FIG. 2B depicts an expanded view of the cell distribution manifold 229. Cell emitters 230 on manifold 229 provide efficient and effective distribution of cells throughout the foam without mechanical agitation as the foam advances through plug-flow reactor 227.

Alternatives to the specific embodiment shown in FIG. 2 are possible. For example, a series of inlet lines could be used to introduce medium components into the reactor as the foam moves through plug-flow reactor 227. Conduit 225 could be replaced by or fitted with a pump to facilitate the movement of foam from foam production chamber 219 in plug-flow reactor 227. And a pump could be used with or instead of valve 240 to transfer the contents of plug-flow reactor 227 into foam collapse chamber 243. These and other variations will be recognized as within the ability of those skilled in the art.

As shown in FIG. 2, the plug-flow mode allows bioprocess reactant additions and/or product removals along the temporal and spatial progression of the plug. Reactants can also or alternatively be added in the foam creation and cell entrainment stages. Such controlled addition and removal of reactants and products can be extremely important in certain bioprocess reactions, because many bioprocesses will only successfully proceed to completion, or proceed at acceptable rates, if certain metabolites, co-metabolites, or synthetic precursors are introduced at particular times during the reaction.

A wide variety of prokaryotic and eukaryotic cells can be used in the biological process of the present invention. Suitable classes of cells include microorganisms such as bacteria, yeast, and fungi, as well as plant and animal (including mammalian) cells.

Suitable yeasts include species from the genera Candida, Hansenula, Torulopsis, Saccharomyces, Pichia, 1-Debaryomyces, Lipomyces, Cryptococcus, Nematospora, and Brettanomyces. The preferred genera include Candida, Hansenula, Torulopsis, Pichia, and Saccharomyces. Examples of suitable species include: *Candida boidinii, Candida mycoderma, Candida utilis, Candida stellatoidea, Candida robusta, Candida claussenii, Candida rugosa, Brettanomyces petrophilium, Hansenula minuta, Hansenula saturnus, Hansenula californica, Hansenula mrakii, Hansenula silvicola, Hansenula polymorpha, Hansenula wickerhamii, Hansenula capsulata, Hansenula glucozyma, Hansenula henricii, Hansenula nonfermentans, Hansenula philodendra, Torulopsis candida, Torulopsis bolmii, Torulopsis versatilis, Torulopsis glabrata, Torulopsis molishiana, Torulopsis nemodendra, Torulopsis nitratophila, Torulopsis pinus, Pichia farinosa, Pichia polymorpha, Pichia membranaefaciens, Pichia pinus, Pichia pastoris, Pichia trehalophila, Saccharomyces cerevisiae, Saccharomyces fragilis, Saccharomyces rosei, Saccharomyces acidifaciens, Saccharomyces elegans, Saccharomyces rouxii, Saccharomyces lactis, Saccharomyces fractum.*

Suitable bacteria include species from the genera Bacillus, Mycobacterium, Actinomyces, Nocardia, Pseudomonas, Methanomonas, Protaminobacter, Methylococcus, Arthrobacter, Methylomonas, Brevibacterium, Acetobacter, Methylomonas, Brevibacterium, Acetobacter, Micrococcus, Rhodopseudomonas, Corynebacterium, Rhodopseudomonas, Microbacterium, Achromobacter, Methylobacter, Methylosinus, and Methylocystis. Preferred genera include Bacillus, Pseudomonas, Protaminobacter, Micrococcus, Arthrobacter and Corynebacterium.

Examples of suitable species include: *Bacillus subtilus, Bacillus cereus, Bacillus aureus, Bacillus acidi, Bacillus urici, Bacillus coagulans, Bacillus mycoides, Bacillus circulans, Bacillus megaterium, Bacillus licheniformis,*

Pseudomonas ligustri, Pseudomonas orvilla, Pseudomonas methanica, Pseudomonas fluorescens, Pseudomonas aeruginosa, Pseudomonas oleovorans, Pseudomonas putida, Pseudomonas boreopolis, Pseudomonas pyocyanea, Pseudomonas methylphilus, Pseudomonas brevis, Pseudomonas acidovorans, Pseudomonas methanoloxidans, Pseudomonas aerogenes, Protaminobacter ruber, Corynebacterium simplex, Corynebacterium hydrocarbooxydans, Corynebacterium alkanum, Corynebacterium oleophilus, Corynebacterium hydrocarboclastus, Corynebacterium glutamicum, Corynebacterium viscosus, Corynebacterium dioxydans, Corynebacterium alkanum, Micrococcus cerificans, Micrococcus rhodius, Arthrobacter rufescens, Arthrobacter parafficum, Arthrobacter citreus, Methanomonas methanica, Methanomonas methanooxidans, Methylomonas agile, Methylomonas albus, Methylomonas rubrum, Methylomonas methanolica, Mycobacterium rhodochrous, Mycobacterium phlei, Mycobacterium brevicale, Nocardia salmonicolor, Nocardia minimus, Nocardia corallina, Nocardia butanica, Rhodopseudomonas capsulatus, Microbacterium ammoniaphilum, Archromobacter coagulans, Brevibacterium butanicum, Brevibacterium roseum, Brevibacterium flavum, Brevibacterium lactofermentum, Brevibacterium paraffinolyticum, Brevibacterium ketoglutamicum, Brevibacterium insectiphilium.

Suitable fungi include species from the genera Aspergillus, Monilia, Rhizopus, Penicillium, Mucor, Alternaria and Helminthosporium.

Examples of suitable species of fungi include: *Aspergillus niger, Aspergillus glaucus, Aspergillus flavus, Aspergillus terreus, Aspergillus itconicus, Penicillium notatum, Penicillium chrysogenum, Penicillium glaucum, Penicillium griseofulvum, Penicillium expansum, Penicillium digitatum, Penicillium italicum, Rhizopus nigricans, Rhizopus oryzae, Rhizopus delemar, Rhizopus arrhizus, Rhizopus stolonifer, Mucor mucedo, Mucor genevensis.*

Examples of bioprocesses which can be carried out using the method and apparatus of the invention include the production of baker's yeast, single-cell protein by Candida, and cheese inoculant by Lactobacilli. The invention is also useful for the production of secretory products, for example, ethanol by Saccharomyces, acetone-butanol by Clostridium, glycerol by Torulopsis and Dunaliella, acetic acid by Acetobacter, fumaric acid by Rhizopus, citric acid by Aspergillus, amino acids by Corynebacterium, renin by Alcaligenes and Pseudomonas, amylases by Bacillus and Neurospora, proteases by Streptomyces and Thermomonospora, lipases by Mucor, erythropoietin by Chinese Hamster Ovary cell lines, interferons by Human Leukocyte cell lines, antibodies by Murine Hybridoma cell lines, and antigens by Human Melanoma cell lines.

Essentially any mammalian cell system that is culturable in vitro may be employed in the method and apparatus of the present invention. Examples of mammalian cell types and cell products are those shown in Table I, below:

TABLE I

| Cell Type | Mammalian Cell Product |
|---|---|
| "OKT3", "CIE3" | Monoclonal antibodies |
| "Namalwa" | Lymphoblastoid interferon |
| "Vero" | Rabies vaccine |
| "Vero" | Polio vaccine |
| heterohybridoma "H-CB-hah-E" | Immunoglobulin G |

Examples of the production of intracellular products which can be carried out using the method and apparatus of the present include the production of nucleosides and nucleotides by Candida or Bacillus, sesquiterpenes by Hyoscamus, pyrrolizidine alkaloids by Nicotiana, steroids by Solanum, terpenes by Mentha, quinones by Rumex, quinolizidines by Lupinus, and tropanes by Atropa.

The present invention can be used in waste treatment applications, for example, molecular breakdown of 2,4,5, Trichlorophenoxyacetic acid and pentachlorophenols by Pseudomonas.

A wide variety of bio-mediated chemical transformations can be carried out using the method and apparatus of the invention. Examples of such transformations are given in Table II, below.

TABLE II

| Starting Material | Product | Organism |
|---|---|---|
| tryptophan | 5 hydroxy-tryptophan | Bacillus |
| 1,7-octadiene | 7,8-epoxy-1-octene | Pseudomonas |
| glaucine | dihydroglaucine | Fusarium |
| napthalene | salicylic acid | Corynebacterium |
| d,1-menthyl laureate | 1-menthol | Mycobacterium |
| D-phenyl-glycine methyl ester | ampicillin | Kluyvera |
| progesterone | 11-alpha-hydroxy-progesterone | Rhizopus |
| cortisol | prednisolone | Arthrobacter |
| progesterone | 1-dehydro-testololactone | Cylindrocarpon |
| glycerol | dihydrooxyacetone | Acetobacter |
| methyl digitoxin | methyl digoxin | Daucus |
| tryptamine | ajmalicine | Cantharanthus |
| sucrose | steroid glycosides | Solanum |

In the present invention, the cells can be present in an aqueous culture medium at a concentration from about $10^1$ cells/ml to about $10^{10}$ cells/ml, preferably from about $10^3$ to about $10^8$ cells/ml, and most preferably from about $10^5$ to about $10^7$ cells/ml. The cells can be maintained at conditions favoring rapid, exponential growth and approximately double their concentration in the aqueous medium. Alternatively, the cells can be maintained at conditions that favor low cell growth and high product formation.

The growth of the cells is sensitive to the operating temperature of the bioreactor and each particular type of cell has an optimum temperature for growth. The broad temperature range employed in the method of the present invention would be from about 20° C. to 65° C. and more preferably between 35° C. and 60° C. The temperature selected will generally depend upon the cells employed in the process, because different cells have somewhat different temperature/growth rate/product formation relationships.

The temperature can be maintained by indirect heat exchange using cooling coils or other means immersed in the foam contained in the bioreactor or surrounding the bioreactor exterior.

In practicing the process of the present invention, suitable nutrient media for many bioprocesses contain assimilable sources of carbon, nitrogen, phosphorus, magnesium, calcium, potassium, sulfur and sodium as well as trace quantities of copper, manganese, molybdenum, zinc, iron, boron, iodine and selenium. As is well known in the art, the relative amounts of the above nutrients can vary depending on the cells selected for the process. The major inorganic nutrients (for example, nitrogen, phosphorus, magnesium, sulfur, potassium) can be employed at concentrations from about 0.1 to about 5.0 weight percent of the culture medium, preferably from about 0.05 to about 1.0 weight percent of each of sulfur, nitrogen, potassium and phosphorus are used. Nutrients such as manganese, copper, boron, iron, zinc, etc. can be supplied at concentrations from 0.001 to about 1.0, preferably 0.01 to about 0.1 weight percent based on the culture medium. The nutrients are preferably supplied as water soluble salts. Examples of these include the alkali metal and ammonium chlorides, sulfates, nitrates, phosphates, as well as the sulfates, nitrates, chlorides of magnesium and any of the molybdate, sodium borate, cupric chloride, zinc sulfate, etc. In addition, the nutrient medium can also contain vitamins as is known in the art when their presence is known to be desirable for the propagation of certain microorganisms. For example, many yeasts appear to require the presence of one or both of biotin and thiamin for their proper propagation. And, as is known to those skilled in the art, animal cells often require undefined media, for example, serum.

For processes utilizing yeasts or fungi, the pH is preferably in the range of approximately 3–5 and, for the utilization of bacteria, the pH should preferably be in the range of approximately 6–7.5. Animal cells typically require a pH in the range of from about 5 to about 8.

To maintain the pH within these optimum ranges, various buffer agents can be incorporated in the aqueous medium, such as alkali metal or ammonium acetates, mono- and di-alkali metal orthophosphates or pyrophosphates, alkali metal citrates, boric acid and alkali metal borates, etc. These can be used in concentrations from about 0.01 to 3.0 weight percent, with the particular buffer system being selected on the basis of the value of the optimum pH desired in the solution. The pH can also be controlled by periodic or continuous addition of an alkaline material such as ammonia, alkali metal hydroxides, etc. in amounts sufficient to correct any deviation from the desired pH value.

The oxygen needed for aerobic processes can be supplied pure or from a free oxygen-containing source such as air which is suitably supplied to the reactor vessel at a pressure of from approximately 0.5 to about 5 atmospheres and preferably from 1 to 2 atmospheres. Oxygen enriched air is a good source of oxygen.

For certain bioprocesses, the method of the present invention will employ an alcohol, a sugar, and/or a gaseous hydrocarbon as the source of carbon and energy for cell growth. Suitable alcohols are straight chain alcohols having from 1 to 16 carbon atoms per molecule. Preferably the alcohol has from 1 to 6 carbon atoms per molecule and more preferably the alcohol will be either ethanol or methanol and most preferably, methanol. Examples of suitable alcohols include methanol, ethanol, 1-propanol, 1-butanol, 1-octanol, 1-dodecanol, 1-hexadecanol, 2-propanol, 2-butanol, 2-hexanol, and the like. Mixtures of alcohols can also be employed if desired. Glucose is an example of a sugar suitable for use as a carbon and energy source.

Suitable hydrocarbons include methane, ethane, propane, butane, pentane, etc. Pure hydrocarbon gas or mixtures of hydrocarbon gases are preferred. If desired, the discontinuous gas phase can be diluted with various inert or moderating materials, e.g., nitrogen, carbon dioxide, etc., which may also be used to dilute an otherwise pure oxygen source. The present invention is also applicable to a process using a hydrocarbon that is liquid at the process conditions.

The duration of processes carried out in accordance with the present invention varies considerably with the activity of the particular cell employed. The process may be continued throughout the period of expontial growth rate of the cells, a period that can be about 1 to about 12 hours. Preferably, the plug-flow time is from about 1 to about 5 hours, and may involve cell recycle. It is important to recognize, however, that in many processes, the rate of product formation is unrelated to the rate of growth of the cells employed. The process times provided herein, therefore, are by way of illustration only.

In preparing the foam, the gaseous agent employed in the discontinuous phase, i.e., either oxygen, an oxygen-containing gas, a gaseous hydrocarbon or a gas containing the gaseous hydrocarbon, or a nitrogenous gas, such as ammonia, is mixed in proportions to the aqueous medium from about 3/1 to about 40/1 volumes per liquid volume. Preferably, the volumetric proportions are from about 5/1 about 20/1, and most preferably from about 7/1 to about 15/1 parts of the discontinuous gas per part by volume of the liquid.

In this regard, it should be noted that the method and apparatus of the invention can be used for biological processes which can deplete or convert noxious gases, for example, in odor control applications. The undesired gas or gases can be fed into the reactor to produce a foam as described above. Cells capable of degrading the gas are entrained in the foam, where they can efficiently use the gas for fuel or convert the gas to a benign product.

Various mechanical techniques can be employed to produce a foam from an aqueous medium and gas. For example, a froth can be produced by admixing the aqueous medium and the gaseous agent(s) under high mechanical agitation or, preferably, the gaseous agent(s) can be injected via an injection nozzle which discharges into the aqueous medium to produce a foam. A variety of suitable injection nozzles are shown in FIGS. 3A through 3K.

Figure 3A:
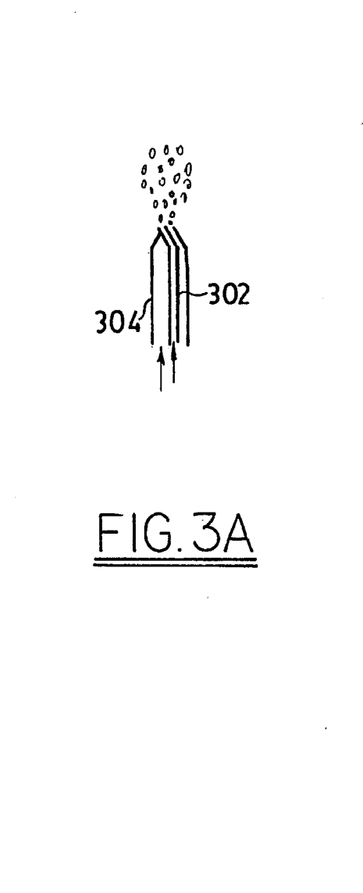
FIGS. 3A through 3K are alternative foam creation nozzles for use in the foam production chamber shown in FIG. 1A.

FIG. 3A is a schematic view of a two-phase nozzle. With this nozzle, gas G and liquid F are fed separately into the foam production chamber through nozzles 302 and 304, respectively.

Figure 3B:
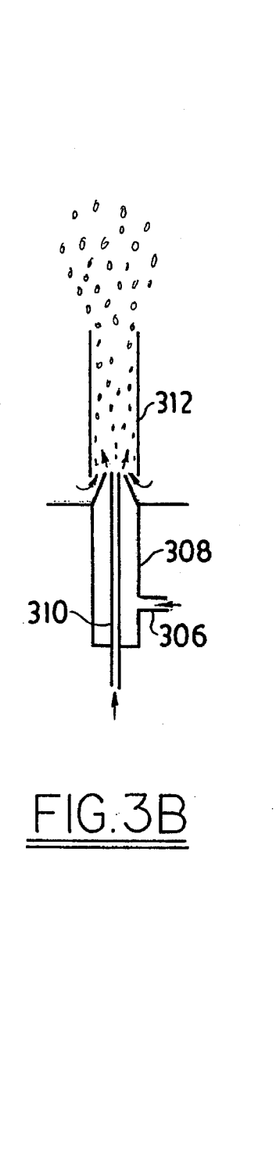

The nozzle shown schematically in FIG. 3B includes an impulse exchange tube. Gas G is injected into chamber 308 via line 306, and mixes with liquid F supplied through line 310 in impulse exchange tube 301.

Figure 3C:
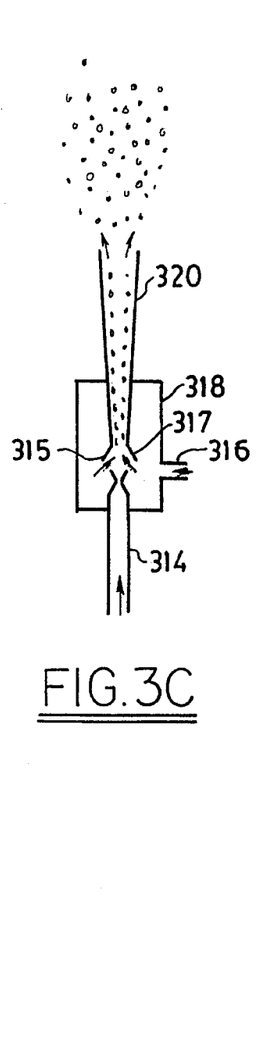

FIG. 3C depicts an ejector nozzle. Gas G is fed through line 316 into housing 318 and ultimately through inlets 315 and 317 into stream of liquid F entering mixing tube 320 via line 314.

Figure 3D:
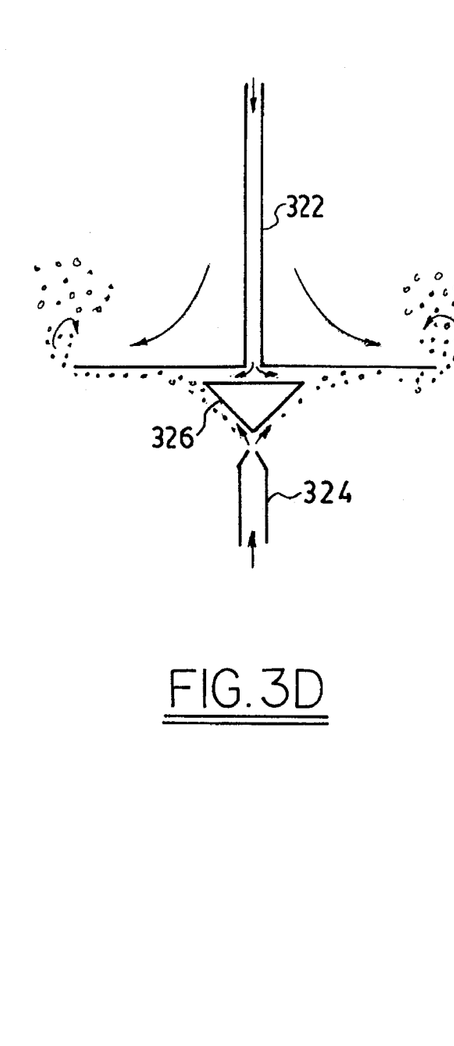

The nozzle shown in FIG. 3D is a radial flow nozzle. Gas G is injected via tube 322 into the liquid F flowing over conical deflector 326 from line 324.

Figure 3E:
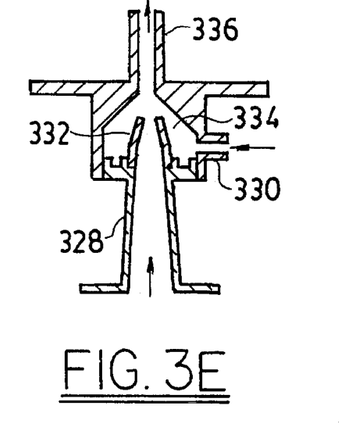

FIG. 3E is a schematic view of an alternative ejector nozzle. Gas G is injected through line 330 into mixing chamber 334, where it mixes with liquid F supplied through tube 328. The foamed mixture of gas and liquid then advances through outlet 336 into the foam production chamber (not shown).

Figure 3F:
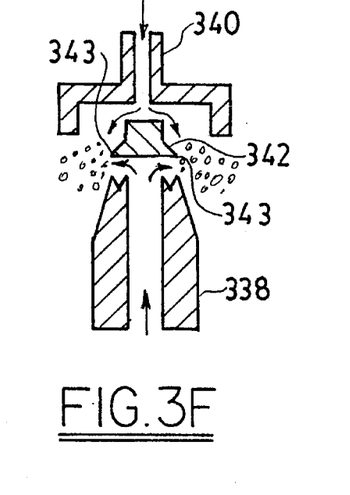

FIG. 3F is a schematic view of an alternative radial flow nozzle. Liquid F supplied through tube 338 is radially distributed via deflector 342. Gas G entering the nozzle via line 340 is similarly deflected via deflector 342 radially. Gas G and liquid F then combine in the vicinity of the outer edge 343 of deflector 342.

Figure 3G:
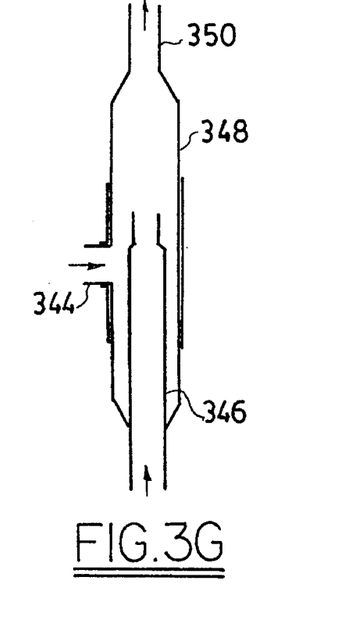

The nozzle shown schematically in FIG. 3G is a two phase nozzle. Liquid F and gas G are injected separately via lines 344 and 346, respectively into outer tube 348. The foamed mixture of gas and liquid then progresses through outlet 350 into the foam production chamber (not shown).

Figure 3H:
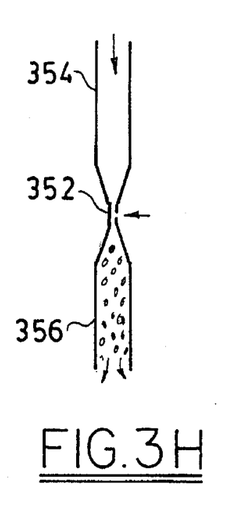
Figure 3I:
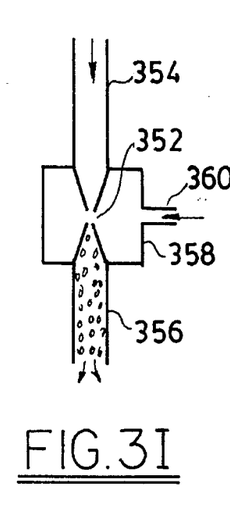

FIGS. 3H and 3I are schematic views of alternative Venturi nozzles. In each, gas G is injected via inlets 352 into a stream of liquid F supplied through tube 354. The nozzle shown in FIG. 3I includes chamber 358 supplied with gas G via line 360. The foamed mixture of gas and liquid flows out of the nozzle via tube 356.

Figure 3J:
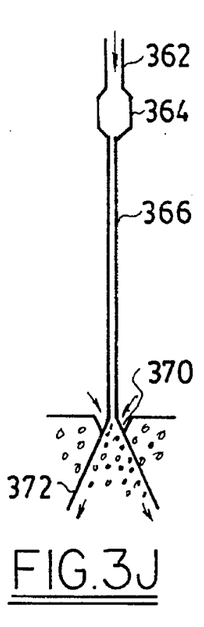
Figure 3K:
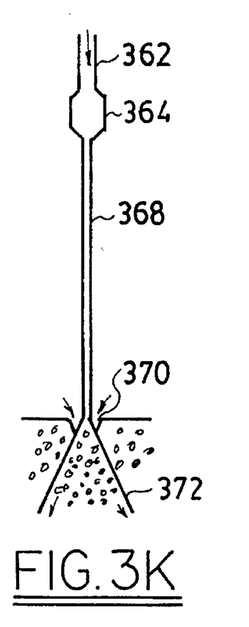

FIGS. 3J and 3K show schematic views of nozzles employing plunging jets of liquid F to create a foam. In FIGS. 3J and 3K, liquid F supplied through line 362 is passed through chamber 364 and then supplied as either a laminar (FIG. 3J) or droplet (FIG. 3K) jet into expansion outlet 372. Liquid F is combined at the entrance to expansion outlet 372 with gas G injected through inlets 370. The mixture of gas and liquid then flows from outlet 372 into either the foam production chamber or into the cell entrainment chamber (not shown).

Figure 4:
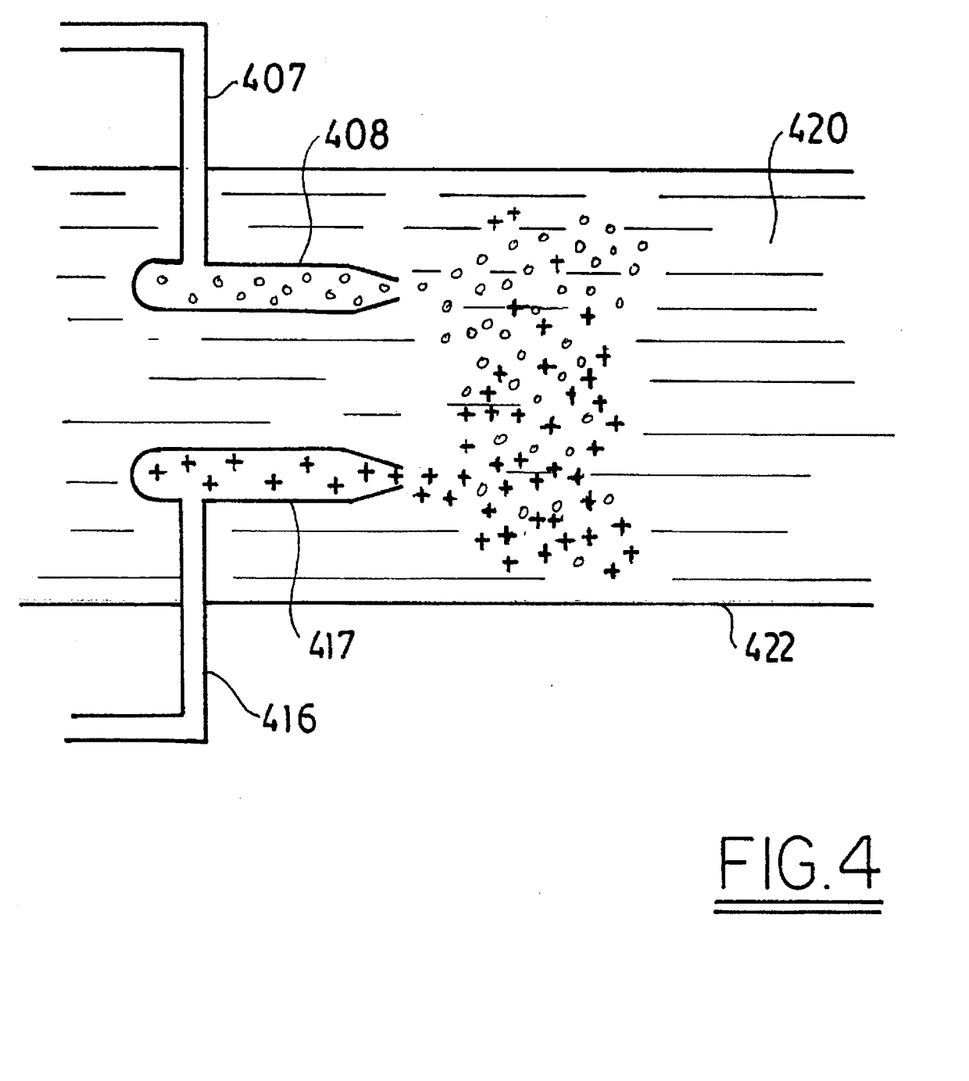
FIG. 4 is a schematic view of a device for introducing admixtures of gases into the foam production chamber shown in FIG. 1A.

FIG. 4 depicts an apparatus for separately introducing gases into a liquid medium to create a foam in accordance with the process of the present invention. Here, gases which must be kept separate but allowed proximity to the cells can be individually delivered through lines 407 and 416 via nozzles 408 and 417, respectively into medium 420.

The stability of the foam can be controlled in various ways. In the preferred method, foaming agents and/or foam stabilizers are employed that will provide foams having stabilities of from 15 minutes to about 7 hours, but which are easily broken when subjected to a pressure change. Suitable foaming agents, such as nonionic, cationic and anionic surfactants, are well known in the art. The foaming agents employed in the method of the invention are preferably biologically inert and non-toxic. The foam stabilizers include any of the well known water soluble polymers and fatty amines which have been used as protective colloids in various aqueous suspension and emulsion techniques.

Various surfactants can be added to lower the surface tension of the water employed, and various water soluble polymers and viscous additives can be added to enhance the viscosity of the water and thereby stabilize the foam.

Various viscous additives can be added to the aqueous medium to increase the viscosity and thereby serve to enhance or stabilize the foam. These viscous additives are a class of water soluble polymers of natural or synthetic origin which are commonly used as protective colloids. These polymers commonly have molecular weights from 10,000 to 5,000,000 and can be naturally occurring materials, e.g., proteins, alginates, cellulose ethers, or entirely synthetic polymers, e.g., polyvinyl alcohol, partially hydrolyzed polyacrylamide, maleic acid or anhydride copolymers, polyvinyl pyrrolidone and copolymers thereof, etc. Mixtures of these may be employed.

The concentration of the surfactant and/or foam stabilizer can be varied to adjust the stability or life of the foam. The various surfactants and stabilizers form foams having varied stability for each surfactant or combination of surfactant(s) and/or stabilizer(s). Generally, however, the surfactants and stabilizers exhibit their maximum effectiveness at concentrations from about 0.5 to 10 weight percent. Within this range, the concentration can also be varied to control the life of the foam. Thus, a blend of about equal amounts of dodecyl benzene sulfonate surfactant and a partially hydrolyzed soybean protein extract can be used at concentrations from 1 to about 15 weight percent to achieve foams having stabilities of from 5 to about 180 minutes, in direct proportion to the concentration of these additives.

The liquid also contains about $10^1$ to about $10^{10}$ cells/ml of a suitable cell described above together with the inorganic nutrients previously described at concentrations from about 1 to 1000 parts per million and sufficient to sustain the cell.

As apparent to those skilled in the art, the surfactant and/or viscous additive to be used should be checked for toxicity to the particular cell that will be used. This can be simply performed by preparing a test culture media of the cell with and without the foaming additives. The culture media are then incubated at their optimum temperature in an atmosphere rich in the gas(es) to be employed in the process. The culture medium is checked for growth or other measure of metabolism, for example, product formation, after several hours to confirm that no inhibition of growth is present in the medium containing the foaming additives.

The foam structure provides an ideal environment for growth of cells. The mass transfer of gaseous reactants into the aqueous phase is enhanced by the very high interfacial surface area obtained in the foam. This environment is maintained with no stirring or mixing so that the high shear forces exerted on cells in previous processes can be reduced to an insignificant amount.

The conditions in the bioreactor can be varied considerably to achieve optimum economical processing. The pressure within the reactor vessel may, for example, be from 1 to about 10 atmospheres, and the gas to liquid volumetric ratio in the foam may, for example, be from 30 to about 50.

Most bioprocesses in accordance with the invention will be done at atmospheric pressure. At the end of the plug-flow reactor section, the foam is pumped into a foam collapse chamber, where it can be subjected to a pressure change.

In one embodiment of the invention, the bubbles of the foam are subjected to a gradual increase in pressure to cause implosion. For example, if the bubbles enter the chamber with an internal pressure of 0 atmospheres, a compressor or cylinder can be used to supply gas to the foam collapse chamber to impose and maintain a pressure of from about 0.1 to about 2 atmospheres in order to slowly and gently collapse the bubbles. Alternatively, the bubbles of the foam may be exploded by application of a vacuum to create a small pressure differential. Various components of the reaction medium may then be separated and recovered, if desired, by allowing the medium to settle into distinct phases which can be separately removed from the foam collapse chamber, for example, or by transferring the reaction medium mixture into a centrifuge or other separation devices such as membrane filters.

Breakage of the foam enables economical recovery of the components of the mixture. In prior biological processes employing foams, mechanical foam breakage techniques have been employed. Mechanical bubble breakage techniques traumatize sensitive biological cells because they exert high shear forces on the cells. Mammalian cells, in particular, are not capable of surviving such trauma.

Breaking the foam in accordance with the present invention avoids the forces which generate cell damage. Carefully controlled destruction of the foam can greatly reduce the stress forces exerted on the cells. In addition, transformation of the foam into distinct phases of liquid, gas, cells, products and related biomass provides the opportunity to further separate these phases and constituents.

The process of the invention, and function of the apparatus in accordance with the invention, are illustrated by the following Examples.

Examples

Example 1—Fungal Production of alpha-hydroxyethyllysergamide

Cell-inoculum is produced by homogenizing mycelium of a 5–10 day agar slant culture of *Claviceps paspali* in a shake flask to produce condia suspension in the following medium: mannitol (40 g/l), succinate (10 g/l), $KH_2PO_4$ (1.0 g/l), $MgSO_4$ $H_2O$ (0.8 g/l), $NaNO_3$ (0.1 g/l), $FeSO_4$ $7H_2O$ (0.05 g/l), $MnSO_4$ $H_2O$ (0.01 g/l), $ZnSO_4$ $7H_2O$ (0.005 g/l), $CuSO_4$ $5H_2O$ (0.005 g/l), $Ca(NO_3)_2$ $4H_2O$ (0.3 g/l). The pH is adjusted to 5.2 with $NH_4OH$. This cell-inoculum broth is incubated for 48 hours at 24° C.

The cell-inoculum broth is introduced (via the cell emitters) into the biofoam reactor downstream of the foam-production chamber in which the following medium has been previously introduced and foamed: mannitol (50 g/l), succinate (30 g/l), KH$_2$PO$_4$ (1.0 g/l), MgSO$_4$ H$_2$O (0.8 g/l), NaNO$_3$ (0.1 g/l), FeSO$_4$ 7H$_2$O (0.05 g/l), MnSO$_4$ H$_2$O (0.01 g/l), ZnSO$_4$ 7H$_2$O (0.005 g/l), CuSO$_4$ 5H$_2$O (0.005 g/l), Ca(NO$_3$)$_2$ 4H$_2$O, pH adjusted to 5.4 with NH$_4$OH.

The foam moves in plug-flow mode through reactor for 24 hours at 25° C.

Upon transfer from the plug-flow section, the foam is transferred to the foam-breakage chamber which imposes a low vacuum, breaking the foam.

The resulting, de-foamed broth which contains cells, spent medium, metabolites, products, residual reactants and all the other components of the bioreactor fluid contents, is transferred to a separation step in which a combination of centrifugation, chromatography and membrane separation are used to separate and purify the product. Cells and other components of the bioreaction process are retained as desired.

Example 2—Mammalian Cells to Produce Immunoglobulin G (IgG)

Inoculum is produced by subculturing murine hybridoma cells (e.g., lines "H-CB-hah E" or "X87") in roller bottles containing RPMI-1640 medium (Gibco, Grand Island, N.Y.) containing 1.0% glutamine, 5.0% Fetal Bovine Serum, trace penicillin and streptomycin. The inoculum is buffered with HEPES, and maintained at 30° C.

The cell-inoculum is introduced (via the cell emitters) into the Biofoam™ reactor, in order to reach a final reactor concentration of approximately 4.5×10$_4$ cells/ml. Introduction of cells is downstream of the foam-production chamber in which the following medium has been previously introduced and foamed with an appropriate surfactant: RPMI-1640 medium (Gibco, Grand Island, N.Y.) containing 1.0% glutamine, 5.0% Fetal Bovine Serum, trace penicillin and streptomycin, buffered with HEPES.

The foam moves in plug-flow mode through reactor such that any "slice" of the reactor contents reside in the plug-flow reactor for a minimum 24 hours. The process is conducted at 25° C. to 35° C.

Upon transfer from the plug-flow section, the foam is transferred to the foam-breakage chamber which imposes a low pressure, breaking the foam through gentle bubble implosion.

The resulting de-foamed broth which contains cells, spent medium, IgG, metabolites, residual reactants and all the other components of the bioreactor fluid contents, is transferred to a separation step in which a combination of centrifugation, chromatography and membrane separation are used to separate and purify the product. Cells and other components of the bioreaction process are retained as desired.

Example 3—Plant Cells to Produce Secondary Metabolite

Cell-inoculum is produced by introducing callous tissue of an in vitro culture of *Lithospermum erythrorhizon* into a shake flask to containing the medium: sucrose (40 g/l), 3-indoleacetic acid (40 mg/l), Na$_2$SO$_4$ (3.0 g/l), Ca(NO$_3$)$_2$ (1.3 g/l), MgSO$_4$ 7H$_2$O (1.5 g/l); FeSO$_4$ 7H$_2$O (0.05 g/l), MnSO$_4$ H$_2$O (0.01 g/l), ZnSO$_4$ 7H$_2$O (0.005 g/l), CuSO$_4$ 5H$_2$O (0.005 g/l), Ca(NO$_3$)$_2$ 4H$_2$O (0.3 g/l), pH adjusted to 6.5 with NH$_4$OH. The inoculum broth is incubated for 48 hours at 25° C.

Cellulase (0.005 g/l) is added to disaggregate the cell clumps.

The cell-inoculum broth is introduced (via the cell emitters) into the biofoam reactor, in order to reach a final reactor concentration of approximately 4.5×10$^4$ cells/ml. Introduction of cells is downstream of the foam-production chamber in which the following medium has been previously introduced and foamed: sucrose (40 g/l), 3-indoleacetic acid (40 mg/l), Na$_2$SO$_4$ (3.0 g/l), Ca(NO$_3$)$_2$ (1.3 g/l), MgSO$_4$ 7H$_2$O (1.5 g/l); FeSO$_4$ 7H$_2$O (0.05 g/l), MnSO$_4$ H$_2$O (0.01 g/l), ZnSO$_4$ 7H$_2$O (0.005 g/l), CuSO$_4$ 5H$_2$O (0.005 g/l), Ca(NO$_3$)$_2$ 4H$_2$O (0.3 g/l), pH adjusted to approximately 7.0 with NaOH or HCl.

The foam moves in plug-flow mode through reactor such that any "slice" of the reactor contents reside in the plug-flow reactor for 48 hours. The process is conducted at 25° C.

Upon transfer from the plug-flow section, the foam is transferred to the foam-breakage chamber which imposes a pressure, breaking the foam through gentle bubble implosion.

The resulting de-foamed broth which contains cells, spent medium, metabolites, products, residual reactants and all the other components of the bioreactor fluid contents, is transferred to a separation step in which a combination of centrifugation, chromatography and membrane separation are used to separate and purify the product. Cells and other components of the bioreaction process are retained as desired.

Example 4—Insect Cells for Production of Intracellular Products

Cell-inoculum is produced by introducing callous tissue of an in vitro culture of Bombyx, or Laspeyresia or Mamestra or Manduca or Spodopter or Culex or Ceratitus or Drosophila or many other insect genera into a shake flask containing the medium: NaH$_2$PO$_4$ H$_2$O (1.45 g/l), KCl (4.6 g/l), CaCl$_2$ 2H$_2$O (1.3 g/l), MgCl$_2$ 6H$_2$O (2.2 g/l), MgSO$_4$ 7H$_2$O (2.7 g/l), NaHCO$_3$ (0.35 g/l), lactalbumin hydrolysate (10.0 g/l), typtose broth 5.0 (g/lH$_2$O); glucose (2.0 g/l), folic acid (1.3 mg/l), biotin (0.21 mg/l), choline chloride (2.0 mg/l), isoinositol (10 mg/l), niacin (0.41 mg/l), thiamine (2.1 mg/l), cyanocobalamin (0.2 mg/l), beta-carotene (0.2 mg/l), streptomycin (100 mg/l). The pH is adjusted to 5.8 with NH$_4$OH. The cell-inoculum broth is incubated for 48 hours at 23° C.

The cell-inoculum broth is introduced (via the cell emitters) into the biofoam reactor, in order to reach a final reactor concentration of approximately 5.0×10$^4$ cells/ml. Introduction of cells is downstream of the foam-production chamber in which the following medium has been previously introduced and foamed: NaH$_2$PO$_4$ H$_2$O (1.45 g/l), KCl (4.6 g/l), CaCl$_2$ 2H$_2$O (1.3 g/l), MgCl$_2$ 6H$_2$O (2.2 g/l), MgSO$_4$ 7H$_2$O (2.7 g/l), NaHCO$_3$ (0.35 g/l), lactalbumin hydrolysate (10.0 g/l), typtose broth 5.0 (g/lH$_2$O); glucose (2.0 g/l), folic acid (1.3 mg/l), biotin (0.21 mg/l), choline chloride (2.0 mg/l), isoinositol (10 mg/l), niacin (0.41 mg/l), thiamine (2.1 mg/l), cyanocobalamin (0.2 mg/l), beta-carotene (0.2 mg/l), streptomycin (100 mg/l).

The foam moves in plug-flow mode through the reactor such that any "slice" of the reactor contents reside in the plug-flow reactor for 48 hours. The process is conducted at 28° C.

Upon transfer from the plug-flow section, the foam is transferred to the foam-breakage chamber which imposes a pressure, breaking the foam through gentle bubble implosion.

The resulting de-foamed broth which contains cells, spent medium, metabolites, products, residual reactants and all the other components of the bioreactor fluid contents, is transferred to a separation step in which a combination of centrifugation, chromatography and membrane separation are used to separate and purify the product. Cells and other components of the bioreaction process are retained as desired.

The process and apparatus of the present invention have significant advantages over prior processes and bioreactors, particularly those employing stirred tank reactors (CSTRs). CSTRs do not work well with high viscosity fluids due to the very high mechanical force required for stirring. The apparatus of the present invention, in contrast, can handle such fluids with ease.

Biological process fluids within CSTRs are also difficult to cool. Cooling in CSTRs is typically accomplished using an external heat-transfer fluid jacket and is problematic due to the small area to volume ratio of the CSTR. In contrast, the apparatus of the present invention may efficiently be cooled using a cooling jacket, as the area to volume ratio of a plug-flow chamber in accordance with the invention is much larger than in a CSTR.

In addition, as discussed above, it is difficult to maintain a sterile environment in a CSTR because the rotating shafts necessarily protrude into the sterile environment. Rotating shaft seals are one of the most common sites of contamination of a biological process carried out in a CSTR. In contrast, the apparatus of the present invention requires fewer seals, valves and nipples than a CSTR, greatly reducing the probability for process-destroying contamination.

CSTRs are also much less efficient in energy consumption than the present apparatus, and require more volume to carry out a biological process than the present apparatus. Also, CSTRs are typically run in batch-mode, requiring an unloading step, while the present process and apparatus may be employed in a continous-flow mode, avoiding the need to shut down a reactor and remove the contents.

A particularly significant advantage of the present invention is its ability to handle a variety of cell types including filamentous microorganisms and cells. Filamentous organisms tend to become entangled in the twisting propeller and shaft of a CSTR, but proceed undisturbed through the plug-flow reactor of the present invention. Also, it appears that anchorage-dependent or surface-dependent cells such as many mammalian cells may be satisfied to be on the surface of bubbles. If so, the apparatus of the present invention could provide the crucial link between fixed film reactors (e.g., hollow fiber reactors for mammalian cell culture) and the ease of processing with a suspended cell system. Many mammalian cells do not thrive in suspension, as such an environment does not provide a suitable substrate to which the cells can attach. For biological processes involving mammalian cells, the method and apparatus of the invention may provide a sufficient "substrate" for the cells (i.e., the bubbles of the foam), while enjoying the flexibility and ease of processing advantages of suspension reactors over fixed film reactors.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A biological process, which involves cell metabolic activity, cell growth, or product formation, comprising:

producing a substantially continuous foam comprising bubbles of a gas in a liquid capable of undergoing a biological process utilizing biological cells;

introducing said cells into said foam after said producing; and maintaining said cells in said foam under conditions effective to carry out said biological process.

2. A process according to claim 1, wherein said maintaining is carried out substantially without mechanical agitation of said foam.

3. A process according to claim 1, further comprising:

subjecting said foam to a pressure change following said maintaining to collapse said foam.

4. A process according to claim 3, wherein said pressure change is an increase in pressure sufficient to collapse said bubbles.

5. A process according to claim 3, wherein said pressure change is a decrease in pressure sufficient to collapse said bubbles.

6. A process according to claim 3, wherein said subjecting is carried out at a controlled rate to avoid stress on said cells.

7. A process according to claim 3, further comprising:

recovering one or more reaction products formed during said process following said subjecting.

8. A process according to claim 3, further comprising:

recovering said cells following said subjecting.

9. A process according to claim 1, wherein said foam moves as a substantially continuous plug along a length of a reactor during said maintaining.

10. A process according to claim 9, further comprising:

adding one or more reactants into said foam during said maintaining.

11. A process according to claim 10, wherein said adding is carried out by introducing the reactants at various locations along the length of said reactor as said foam moves through it.

12. A process according to claim 1, wherein said liquid comprises water, one or more low molecular weight hydrocarbons or alcohols, one or more nutrients, one or more foam-control agents, and mixtures thereof.

13. A process according to claim 1, wherein said cells are selected from the group consisting of bacterial, yeast, fungi, plant and animal cells, and mixtures thereof.

14. A process according to claim 1, further comprising:

collapsing said foam without mechanical agitation of said foam.

15. A process for recovering a reaction product from a biological process, which involves cell metabolic activity, cell growth, or product formation, comprising:

maintaining biological cells in a culture medium, wherein said culture medium comprises a substantially continuous foam comprising bubbles of a gas in a liquid capable of undergoing a biological process utilizing said cells;

subjecting said foam to a change in reaction pressure following said maintaining to collapse said foam; and separating said reaction product from said culture medium following said subjecting.

16. A process according to claim 15, further comprising:

recovering said cells from said culture medium following said subjecting.

17. A process according to claim 15, wherein said maintaining is carried out substantially without mechanical agitation of said foam.

18. A process according to claim 15, wherein said foam moves as a substantially continuous plug along a length of a reactor during said maintaining.

19. A process according to claim 15, wherein said pressure change is an increase in pressure sufficient to collapse said foam.

20. A process according to claim 15, wherein said pressure change is a decrease in pressure sufficient to collapse said foam.

21. A process according to claim 15, wherein said subjecting is carried out at a controlled rate to reduce stress on said cells.

* * * * *